United States Patent
Shelchuk

(10) Patent No.: US 9,414,754 B1
(45) Date of Patent: *Aug. 16, 2016

(54) SYSTEMS AND METHODS FOR EVALUATING VENTRICULAR DYSSYNCHRONY USING ATRIAL AND VENTRICULAR PRESSURE MEASUREMENTS OBTAINED BY AN IMPLANTABLE MEDICAL DEVICE

(75) Inventor: Anne M. Shelchuk, Cupertino, CA (US)

(73) Assignee: PACESETTER, INC., Sylmar, CA (US)

( * ) Notice: Subject to any disclaimer, the term of this patent is extended or adjusted under 35 U.S.C. 154(b) by 631 days.

This patent is subject to a terminal disclaimer.

(21) Appl. No.: 13/207,302

(22) Filed: Aug. 10, 2011

Related U.S. Application Data

(63) Continuation of application No. 11/557,887, filed on Nov. 8, 2006, now Pat. No. 8,016,764.

(51) Int. Cl.
  *A61B 5/02* (2006.01)
  *A61B 5/021* (2006.01)
  *A61B 5/0452* (2006.01)

(52) U.S. Cl.
  CPC .............. *A61B 5/021* (2013.01); *A61B 5/02108* (2013.01); *A61B 5/0452* (2013.01); *A61M 2230/04* (2013.01)

(58) Field of Classification Search
  USPC .................................................. 600/481–508
  See application file for complete search history.

(56) References Cited

U.S. PATENT DOCUMENTS

| | | | |
|---|---|---|---|
| 5,476,483 A | 12/1995 | Bornzin et al. | |
| 6,128,534 A | 10/2000 | Park et al. | |
| 6,480,733 B1 | 11/2002 | Turcott | |
| 6,512,952 B2 | 1/2003 | Stahmann et al. | |
| 6,512,953 B2 | 1/2003 | Florio et al. | |
| 6,527,729 B1 | 3/2003 | Turcott | |
| 6,572,557 B2 | 6/2003 | Tchou et al. | |
| 6,622,045 B2 | 9/2003 | Snell et al. | |
| 6,628,988 B2 | 9/2003 | Kramer et al. | |
| 6,643,546 B2 | 11/2003 | Mathis et al. | |

(Continued)

FOREIGN PATENT DOCUMENTS

| | | |
|---|---|---|
| WO | 03089056 A1 | 10/2003 |
| WO | 2004078254 A2 | 9/2004 |

OTHER PUBLICATIONS

Restriction Requirement mailed on Aug. 20, 2010; U.S. Appl. No. 11/557,887;—Parent Case.

(Continued)

*Primary Examiner* — Etsub Berhanu
*Assistant Examiner* — Karen Toth

(57) ABSTRACT

Techniques are provided for exploiting left atrial pressure (LAP) measurements to determine various ventricular mechanical and electromechanical contraction intervals and for evaluating ventricular dyssynchrony based on those intervals. In one example, LAP measurements are combined with right ventricular pressure (RVP) measurements to determine the interventricular mechanical delay, which is the primary parameter representative of ventricular dyssynchrony. Other intervals determined based, in part, on LAP measurements include the electromechanical delay for the left ventricle (LV), as well as the LV systolic and diastolic intervals. Techniques are also described herein for detecting various RV intervals including the electromechanical delay for the RV, as well as the RV systolic and diastolic intervals.

6 Claims, 13 Drawing Sheets

(56) References Cited

U.S. PATENT DOCUMENTS

| | | |
|---|---|---|
| 6,643,548 B1 | 11/2003 | Mai et al. |
| 6,658,292 B2 | 12/2003 | Kroll et al. |
| 6,666,826 B2 | 12/2003 | Salo et al. |
| 6,741,885 B1 | 5/2004 | Park et al. |
| 6,915,162 B2 | 7/2005 | Noren et al. |
| 6,922,587 B2 | 7/2005 | Weinberg |
| 6,934,586 B2 | 8/2005 | Struble et al. |
| 6,942,622 B1 | 9/2005 | Turcott |
| 8,016,764 B1 * | 9/2011 | Shelchuk ........... 600/486 |
| 2002/0016549 A1 * | 2/2002 | Mejia ................. 600/509 |
| 2003/0055345 A1 | 3/2003 | Eigler et al. |
| 2003/0199934 A1 | 10/2003 | Struble et al. |
| 2004/0019365 A1 * | 1/2004 | Ding et al. ........... 607/17 |
| 2004/0106874 A1 | 6/2004 | Eigler et al. |
| 2004/0167580 A1 * | 8/2004 | Mann et al. ........... 607/17 |
| 2004/0172077 A1 | 9/2004 | Chinchoy |
| 2006/0009810 A1 | 1/2006 | Mann et al. |
| 2006/0149155 A1 | 7/2006 | Hedberg |
| 2006/0149331 A1 | 7/2006 | Mann et al. |
| 2006/0293714 A1 * | 12/2006 | Salo et al. ............ 607/9 |
| 2008/0287818 A1 * | 11/2008 | Shelchuk et al. ...... 600/509 |
| 2010/0049063 A1 * | 2/2010 | Dobak, III .......... 600/508 |

OTHER PUBLICATIONS

NonFinal Office Action mailed on Dec. 7, 2010; U.S. Appl. No. 11/557,887;—Parent Case.

Notice of Allowance mailed on May 12, 2011; U.S. Appl. No. 11/557,887;—Parent Case.

* cited by examiner

SYSTEMS AND METHODS FOR EVALUATING VENTRICULAR DYSSYNCHRONY USING ATRIAL AND VENTRICULAR PRESSURE MEASUREMENTS OBTAINED BY AN IMPLANTABLE MEDICAL DEVICE

CROSS REFERENCE TO RELATED APPLICATIONS

This application is a continuation of copending U.S. patent application Ser. No. 11/557,887, filed Nov. 8, 2006, titled "Systems And Methods For Evaluating Ventricular Dyssynchrony Using Atrial And Ventricular Pressure Measurements Obtained By An Implantable Device."

FIELD OF THE INVENTION

The invention generally relates to implantable medical devices, such as pacemakers or implantable cardioverter/defibrillators (ICDs), and in particular to techniques for evaluating ventricular dyssynchrony within heart failure patients and for controlling therapy in response thereto.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in thickness in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure is often associated with electrical signal conduction defects within the heart. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, the Bundle of His, the right and left bundle branches, with final distribution to the distal myocardial terminals via the Purkinje fiber network. Any of these conduction pathways may potentially be degraded. A common conduction defect arising in connection with CHF is left bundle branch block (LBBB). The left bundle branch forms a broad sheet of conduction fibers along the septal endocardium of the left ventricle and separates into two or three indistinct fascicles. These extend toward the left ventricular apex and innervate both papillary muscle groups. The main bundle branches are nourished by septal perforating arteries. In a healthy heart, electrical signals are conducted more or less simultaneously through the left and right bundles to trigger synchronous contraction of both the septal and postero-lateral walls of the left ventricle. LBBB occurs when conduction of electrical signals through the left bundle branch is delayed or totally blocked, thereby delaying delivery of the electrical signal to the left ventricle and altering the sequence of activation of that ventricle. The impulse starts in the right ventricle (RV) and crosses the septum causing the interventricular septum to depolarize and hence, contract, first. The electrical impulse continues to be conducted to the postero-lateral wall of the left ventricle causing its activation and depolarization but, due to an inability to use the native conduction system, this activation and contraction is delayed. As such, the posterolateral wall of the left ventricle (LV) only starts to contract after the interventricular septum has completed its contraction and is starting to relax. LBBB thus results in an abnormal activation of the left ventricle inducing desynchronized ventricular contraction (i.e. ventricular dyssynchrony) and impairment in cardiac performance.

Degeneration of the electrical conduction system as manifested by LBBB or other conduction defects may come from an acute myocardial infarction but is usually associated with the degeneration as a result of chronic ischemia, left ventricular hypertension, general aging and calcification changes and stretch, especially any form of cardiac myopathy that results in overt CHF. Present treatments are directed towards correcting this electrical correlate by pacing on the left side of the heart and/or pacing on both sides of the left ventricle (lateral-posterior wall and septum) to improve contractile coordination. One particular technique for addressing LBBB is cardiac resynchronization therapy (CRT), which seeks to normalize asynchronous cardiac electrical activation and the resultant asynchronous contractions by delivering synchronized pacing stimulus to both sides of the ventricles using pacemakers or ICDs equipped with biventricular pacing capability, i.e. CRT seeks to reduce or eliminate ventricular dyssynchrony. Ventricular stimulus is synchronized so as to help to improve overall cardiac function. This may have the additional beneficial effect of reducing the susceptibility to life-threatening tachyarrhythmias. With CRT, pacing pulses are delivered directly to the left ventricle in an attempt to ensure that the left ventricular myocardium will contract more uniformly. CRT may also be employed for patients whose nerve conduction pathways are corrupted due to right bundle branch block (RBBB) or due to other problems such as the development of scar tissue within the myocardium following a myocardial infarction. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

With conventional CRT, an external Doppler-echocardiography system may be used to noninvasively assess cardiac function. It can also be used to assess the effectiveness of any programming changes on overall cardiac function. Then, biventricular pacing control parameters of the pacemaker or ICD are adjusted by a physician using an external programmer in an attempt to synchronize the ventricles and to optimize patient cardiac function. For example, the physician may adjust the interventricular pacing delay, which specifies the time delay between pacing pulses delivered to the right and left ventricles, in an attempt to maximize cardiac output. To assess the effectiveness of any programming change, Doppler-echocardiography, impedance cardiography or some other independent measure of cardiac function is utilized.

However, this evaluation and programming requires an office visit and is therefore a timely and expensive process. It also restricts the evaluation to a resting state, commonly with the patient in a supine position. As such, the system is not necessarily optimized for activity, for the upright position, for other times of day since there may also be a circadian rhythm to cardiac function. Also, heart rate and blood pressure have diurnal or circadian variations. Moreover, when relying on any external hemodynamic monitoring system, the control parameters of the pacemaker or ICD cannot be automatically adjusted to respond to on-going changes in patient cardiac function.

Accordingly, it is desirable to configure the implanted device to automatically and frequently adjust the CRT pacing parameters to reduce the degree of dyssynchrony and improve cardiac output. For the implanted device to adjust CRT pacing parameters effectively, the device should have accurate information regarding the current degree of ventricular dyssynchrony and related cardiac parameters. In particular, the device should have accurate and current information pertaining to each of the following:

the "interventricular delay"—the time delay between contraction of the left and right ventricles;
the "intraventricular electromechanical delay for the RV"—the time interval between electrical activation of the RV and actual contraction of the RV;
the "intraventricular electromechanical delay for the LV"—the time interval between electrical activation of the LV and the actual contraction of the LV;
the "LV systolic interval"—the interval during which the LV contracts;
the "RV systolic interval"—the interval during which the RV contracts;
the "LV diastolic interval"—the interval during which the LV relaxes;
the "RV diastolic interval"—the interval during which the RV relaxes.

Of these parameters, the interventricular delay, the systolic intervals, and the diastolic intervals are referred to herein as "mechanical intervals" since these parameters pertain to actual physical contraction of the ventricular chambers. In contrast, the intraventricular delays for the RV and LV are referred to herein as "electromechanical delays" since these parameters pertain to intervals between electrical activation and subsequent mechanical contraction.

Unfortunately, conventional pacemakers and ICDs are not capable of detecting the aforementioned mechanical and electromechanical parameters. That is, although conventional devices are certainly capable of sensing electrical cardiac signals such as P-waves, R-waves, and T-waves, the devices are not typically capable of sensing actual mechanical contraction of the various chambers of the heart and hence cannot detect the mechanical and electromechanical parameters needed for optimal CRT control. Some state-of-the-art pacemakers have been equipped with acoustic sensors to detect heart sounds representative of at least some mechanical cardiac parameters. See, for example, U.S. patent application Ser. No. 10/346,809 of Min et al., filed Jan. 17, 2003 and entitled "System and Method for Monitoring Cardiac Function via Cardiac Sounds using an Implantable Cardiac Stimulation Device". Although the techniques of Min et al. are quite useful, the various parameters specific to ventricular dyssynchrony noted above are not detected by those techniques.

In addition, some attempts have been made to use pressure sensors implanted within the ventricles to detect at least some parameters relevant to ventricular dyssynchrony. See, for example, U.S. Published Patent Application 2003/0199934 of Struble et al. entitled "Cardiac Resynchronization with Adaptive A1-A2 and/or V1-V2 Intervals" and U.S. Published Patent Application 2004/0172077 of Chinchoy entitled "Method and Apparatus for Evaluating and Optimizing Ventricular Synchronization". Struble et al. describes, inter alia, the use of ventricular pressure sensors to determine the time interval between left and right ventricular ejection (as determined based on the upstroke of left and right ventricular pressure measurements.) In particular, left ventricular pressure (LVP) and right ventricular pressure (RVP) measurements are compared to detect the time interval between left and right ventricular ejection. However, reliable detection of LVP is problematic and so it would be desirable to provide alternative techniques for determining the interventricular delay that do not necessarily require an LVP sensor. Also, Struble et al. does not appear to provide techniques for detecting each of the various other ventricular mechanical and electromechanical parameters listed above by exploiting pressure measurements. (Note that Struble et al. also mentions that atrial pressure sensors can be used to determine the time interval between left and right atrial ejection but does not appear to suggest that a combination of atrial and ventricular pressure measurements can be used to detect the interventricular delay or any other parameters specifically pertinent to ventricular dyssynchrony.) The Chinchoy application also describes techniques that exploit both RVP and LVP measurements for use in controlling CRT.

See, also, U.S. Published Patent Application 2006/0009810 of Mann et al. entitled "Method for Detecting, Diagnosing, and Treating Cardiovascular Disease", which describes, inter alia, various techniques for exploiting left atrial pressure (LAP) measurements to determine various parameters and to evaluate cardiovascular disease. For example, Mann et al. describes techniques for calculating a mechanical atrioventricular (A-V) delay interval based, at least in part, on LAP measurements. The Mann et al. application also describes techniques for evaluating the shapes, relative sizes and intervals between various features of the LAP, such as "a-waves", "c-waves" and "v-waves", for use in detecting and diagnosing changes in the severity of various cardiovascular diseases. In one example, an increase in v-wave amplitude along with the merging of the v-wave with the c-wave is deemed to be usually indicative of acute mitral valve regurgitation. However, Mann et al. does not appear to set forth techniques for measuring the interventricular delay as well as the various other ventricular mechanical and electromechanical intervals listed above that are pertinent to ventricular dyssynchrony.

Accordingly, it would be desirable to provide improved techniques for allowing an implantable medical device such as a pacemaker or ICD to directly evaluate ventricular dyssynchrony for use in controlling CRT. In this regard, it is desirable to provide techniques for detecting each of the various parameters listed above that are especially pertinent to ventricular dyssynchrony. It also particularly desirable to provide techniques that permit the interventricular delay to measured without necessarily requiring detection of LVP. It is to these ends that aspects of the invention are directed.

SUMMARY OF THE INVENTION

Systems and methods are provided for use with an implantable medical device for determining ventricular contraction intervals wherein a LAP signal is detected and then at least one ventricular contraction interval is determined based in part on the LAP signal. In other words, certain ventricular mechanical and electromechanical contraction intervals such as the interventricular mechanical delay, the LV systolic interval and the intraventricular electromechanical delay for the LV are determined based on atrial pressure measurements, alone or in combination with other detected parameters. The method may be extended by additionally detecting a RVP signal so as to permit a determination to be made of certain right ventricular delay intervals such as the RV systolic and RV diastolic intervals, as well as the intraventricular electromechanical delay for the RV.

The interventricular mechanical delay is the primary parameter representative of ventricular dyssynchrony. In one example, to determine the interventricular mechanical delay and thereby evaluate ventricular dyssynchrony, the device detects LAP using a pressure sensor implanted in or on the left atrium and then identifies the c-wave therein. The device also detects the RVP using a pressure sensor implanted in or on the RV and identifies an upstroke point therein. The interventricular mechanical delay is then determined based on the time interval between the upstroke of the RVP and the c-wave of the LAP. By determining the interventricular delay based only on LAP and RVP, no LVP sensor is required. Alternatively, if an LVP sensor is also implanted, the LAP-based technique provides an independent procedure for assessing the interventricular delay (in addition to any LVP/RVP measurements) so as to provide a more robust overall determination of the interventricular delay.

To determine the LV systolic interval, the device detects LAP and identifies both the c-wave and the v-wave therein. The LV systolic interval is then determined based on the time interval between the c-wave and the v-wave of the LAP (i.e. the c-v interval). Hence, the LV systolic interval may be determined based solely on an examination of LAP without requiring any ventricular pressure sensors. To determine the LV diastolic interval, the device additionally detects the LV intracardiac electrogram (LV IEGM) and identifies the $R_L$-$R_L$ interval. The LV diastolic interval is then determined based on the difference between the $R_L$-$R_L$ interval of the LV IEGM and the c-v time interval of the LAP. Hence, the LV diastolic interval may be determined based on an examination of LAP and LV IEGM, again without requiring any ventricular pressure sensors.

To determine the intraventricular electromechanical delay for the LV, the device detects the LV IEGM and identifies R-waves therein. The device also detects LAP and identifies c-waves. The intraventricular electromechanical delay for the LV is then determined based on the time interval between the R-wave of the LV IEGM and the c-wave of the LAP. Hence, the intraventricular electromechanical delay for the LV may be determined based on an examination of LAP and the LV IEGM, again without requiring any ventricular pressure sensors.

Assuming an RVP sensor is provided, the implanted device may additionally determine the intraventricular electromechanical delay for the RV, as well as the RV systolic and diastolic intervals, based on RVP and IEGM signals. Briefly, the device detects the RV IEGM and identifies R-waves therein while also detecting RVP and identifying upstroke and downstroke points therein. The intraventricular electromechanical delay for the RV is then determined based on a time interval between the R-wave of the RV IEGM and the upstroke of the RVP. The RV systolic interval is determined by based on a difference between the upstroke and downstroke points of the RVP signal. The RV diastolic interval is determined by additionally evaluating the $R_R$-$R_R$ interval of the RV IEGM. More specifically, the RV diastolic interval is determined based on the difference between the $R_R$-$R_R$ interval and the time interval between the upstroke point and a downstroke point of the RVP signal.

Hence, the various ventricular mechanical and electromechanical parameters are conveniently detected by an implantable medical device based LAP measurements, alone or in combination with other signals, such as LV and RV IEGM signals as well as RVP measurements. None of the parameters requires detection of LVP by the implanted device. These measurement techniques may be advantageously employed alone or in combination with other measurement techniques to provide for a robust overall ventricular dyssynchrony evaluation procedure. Preferably, therapy delivered by the implanted device is controlled based on the various detected parameters. For example, the interventricular pacing delay (i.e. the $V_L$—pulse $V_R$ pulse pacing delay) may be automatically adjusted in accordance with CRT techniques so as to reduce the interventricular mechanical delay. If the patient is know to have diastolic heart failure, pacing may be delivered so as to reduce the measured electromechanical delays while also reducing the LV and RV systolic intervals. Appropriate diagnostic information pertaining to the various detected parameters is preferably stored within the implanted device for subsequent review by the clinician or relayed directly to the clinician via a bedside monitor network or other suitable communication network. The diagnostic information may also be used to track the progression or regression of heart failure or other cardiovascular diseases.

Hence, an effective LAP-based ventricular dyssynchrony evaluation system is provided.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
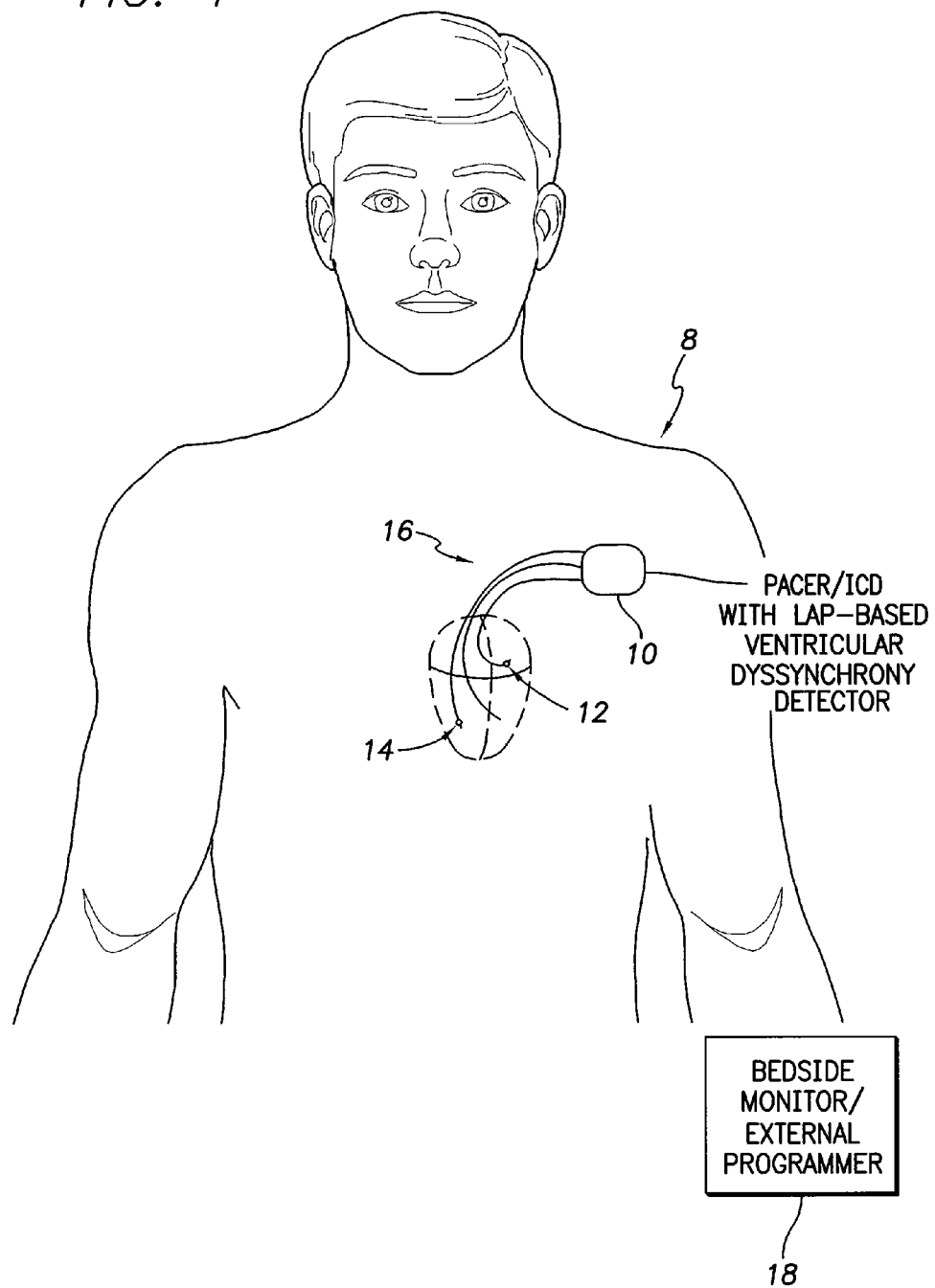
FIG. 1 illustrates pertinent components of an implantable medical system having a pacer/ICD equipped with an LAP-based ventricular dyssynchrony detector.

FIG. 1 illustrates an implantable medical system 8 capable of detecting parameters representative of ventricular dyssynchrony based, in part, on LAP measurements and also for controlling delivery of appropriate therapy in response thereto. To this end, a pacer/ICD 10 (or other implantable medical device) receives signals representative of LAP from an LAP sensor 12 implanted in or on the left atrium or from any other implanted device capable of detecting LAP (such as an epicardial LAP detector or the like.) Depending upon the particular parameters to be detected, the pacer/ICD may also process signals from an RVP sensor 14 implanted in or on the RV. The LAP and RVP sensors are shown mounted to a set of cardiac pacing/sensing leads 16. A more detailed illustration of the leads is provided in FIG. 13 (described below). The leads also include various electrodes from which the pacer/ICD receives electrical cardiac signals for use in controlling pacing therapy and other forms of electrical stimulation therapy. In particular, electrical cardiac signals are separately sensed using RV and LV electrodes from which RV IEGM and LV IEGM signals are derived. RV electrodes may be implanted in the RV itself. LV electrodes are preferably implanted adjacent the LV. In one example, one or more LV electrodes are implanted along the epicardial surface using, for example, a cardiac vein lead implanted via the coronary sinus (CS) or by directly, surgically, screwing electrodes into the LV epicardium. (The use of an LV tip electrode of a cardiac vein/CS lead to sense LV IEGM signals is described below in connection with FIG. 12.) Again, see the descriptions below of FIG. 13 for further details. Depending upon the particular ventricular dyssynchrony parameters to be detected, the pacer/ICD may exploit the RV IEGM and/or LV IEGM signals as well as the aforementioned pressure measurements.

Based on the detected ventricular dyssynchrony parameters, the pacer/ICD automatically controls therapeutic pacing in an attempt to reduce and preferably minimize the degree of dyssynchrony. In this regard, otherwise conventional CRT pacing techniques may be exploited, with the various parameters defining the CRT pacing regime controlled based on any or all of the various detected ventricular dyssynchrony parameters. Additionally, the pacer/ICD performs other standard operations, such as delivering demand based atrial or ventricular pacing, overdrive pacing therapy, antitachycardia pacing (ATP). The pacer/ICD also monitors for atrial or ventricular fibrillation and delivers cardioversion or defibrillation shocks in response thereto.

Diagnostic information is stored within the pacer/ICD for subsequent transmission to an external programmer and/or bedside monitor 18 from which the information may be relayed to a physician or other clinician for review. The diagnostic information preferably includes the various parameters representative of ventricular dyssynchrony detected by the pacer/ICD as well as information pertaining to any changes made to therapeutic pacing parameters, such as CRT parameters. External programmers are typically used only during follow-up sessions with the patient wherein a clinician downloads information from the implanted device, reviews the information and then adjusts the control parameters of the implanted device, if needed, via the programmer. Bedside monitors typically download information more frequently, such as once per evening and can be equipped to relay the most pertinent information to the patient's physician via a communication network. A system incorporating bedside monitoring units connected to a centralized external programmer system is described in U.S. Pat. No. 6,622,045 to Snell et al., "System and Method for Remote Programming of Implantable Cardiac Stimulation Devices".

The pacer/ICD may also monitor changes in the degree of ventricular dyssynchrony and generate warning signals if a significant progression of ventricular dyssynchrony is detected, as such may be indicative of a significant progression of heart failure or other cardiovascular diseases. The warning signals are routed through the bedside monitor to the physician. In this manner, if a significant progression in ventricular dyssynchrony is detected, the physician can be notified to take corrective action.

Overview of LAP-Based Ventricular Dyssynchrony Evaluation Techniques

Figure 2:
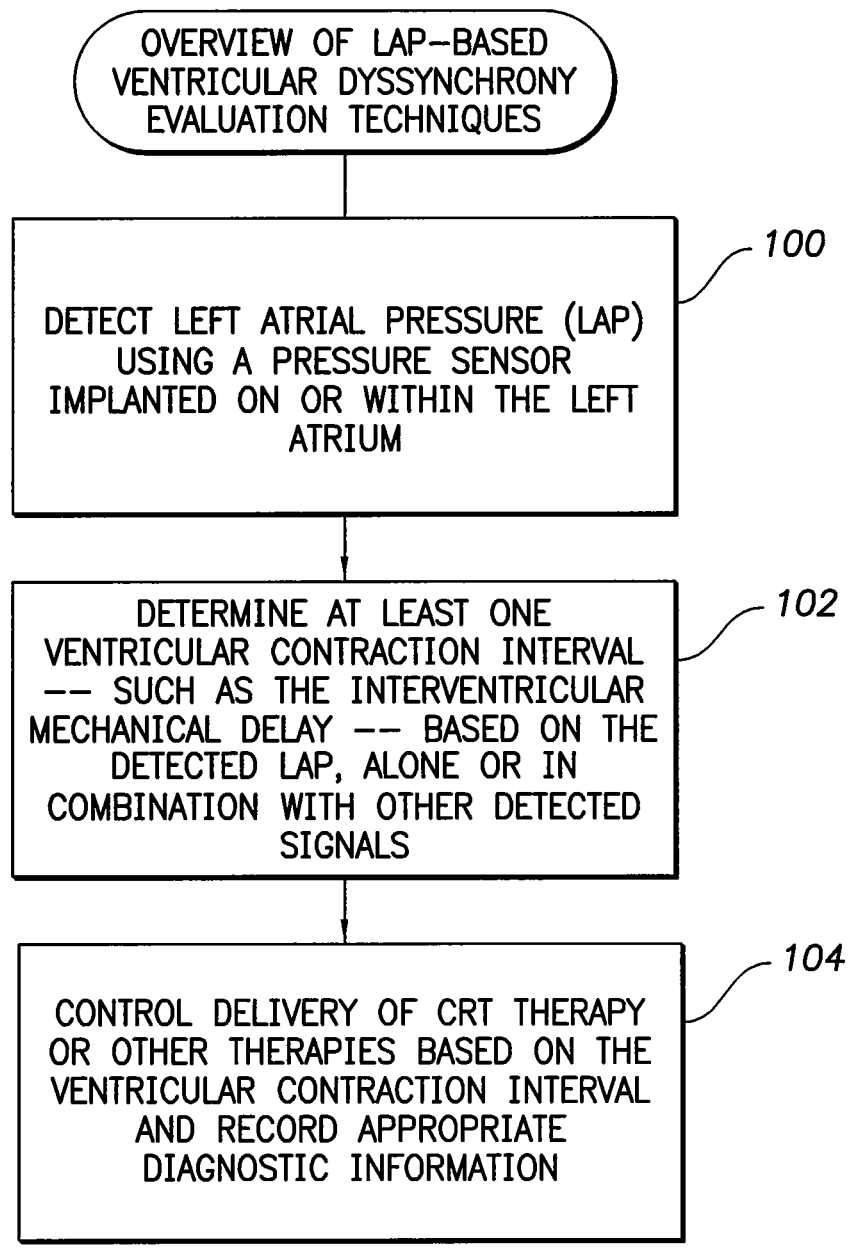
FIG. 2 provides an overview of the LAP-based method for evaluating ventricular dyssynchrony performed by the system of FIG. 1.

FIG. 2 provides a broad overview of the LAP-based techniques of the invention for use in detecting and evaluating ventricular dyssynchrony, which may be performed by the pacer/ICD of FIG. 1 or other suitable device. Briefly, beginning at step 100, the pacer/ICD detects the LAP. Any suitable LAP detection technique may be used. See, for example, U.S. Published Patent Application 2003/0055345 of Eigler et al., entitled "Permanently Implantable System and Method for Detecting, Diagnosing and Treating Congestive Heart Failure". LAP sensors are also discussed in U.S. Published Patent Application 2006/0149155 of Hedberg, entitled "Detection of Diastolic Heart Failure". See also, the above-referenced patent application to Mann et al. as well as U.S. Published Patent Application 2006/0149331 also to Mann et al., entitled "Method for Digital Cardiac Rhythm Management".

At step 102, the pacer/ICD determines at least one ventricular contraction interval—such as the interventricular mechanical delay or the LV systolic and diastolic intervals—based on the detected LAP, alone or in combination with other detected signals or parameters. Various LAP-based detection examples for detecting ventricular mechanical contraction intervals are described below with reference to FIGS. 3-7. Examples involving detection of ventricular electromechanical contraction intervals, particularly the intraventricular electromechanical delays for the LV and RV are described below with reference to FIGS. 8-9. Still further, the pacer/ICD may equipped detect certain RV contraction intervals that do not rely on LAP, such as the RV systolic and RV diastolic intervals, as described below with reference to FIGS. 10-11.

Finally, at 104, the pacer/ICD control delivery of CRT therapy or other therapies based on the detected ventricular contraction interval. In particular, the pacer/ICD may adjust an interventricular pacing delay (i.e. a $V_L$-pulse—$V_R$ pulse pacing delay) to reduce ventricular dyssynchrony. AV pacing delays may also be selectively adjusted (i.e. $A_R$-pulse—$V_R$ pulse and $A_R$-pulse—$V_L$ pulse pacing delays). In at least some cases, adjustment of these parameters may be performed in conjunction with other pacing delay optimization techniques. See, for example, techniques described in U.S. patent application Ser. No. 10/928,58, of Bruhns et al., filed Aug. 27, 2004, entitled "System and Method for Determining Optimal Atrioventricular Delay based on Intrinsic Conduction Delays", U.S. patent application Ser. No. 11/199,619, filed Aug. 8, 2005, of Gill et al., entitled "System And Method For Determining Preferred Atrioventricular Pacing Delay Values Based On Intracardiac Electrogram Signals", and U.S. patent application Ser. No. 11/366,930, of Muller et al., filed Mar. 1, 2006, entitled "System and Method for Determining Atrioventricular Pacing Delay Based on Atrial Depolarization". Other therapeutic techniques may be employed that do not necessarily involve adjusting pacing parameters. See, for example, U.S. patent application Ser. No. 11/136,791 of Kroll et al., filed May 25, 2005, entitled "Synaptic Pacing for Treating Cardiac Conduction Defects Using an Implantable Medical Device."

The pacer/ICD also records appropriate diagnostic information including values of the particular ventricular contraction intervals or other intervals that have been detected. Trend information pertaining to changes in the various parameters may also be stored. If the pacer/ICD is so equipped, histogram-based techniques for reducing the amount of data that needs to be stored for trending purposes may be advantageously employed. See, for example, techniques described in U.S. patent application Ser. No. 11/397,066, of Koh, filed Apr. 3, 2006, entitled "HF Trending Parameter for Screening Out Dilated Cardiomyopathy by Circadian Based R-R Histogram Deviation from the Daily Mean". As already explained, the diagnostic data may be transmitted to an external device, such as a bedside monitor or external programmer for subsequent review by a clinician. Warning signals may be generated in response to any significant increase in ventricular dyssynchrony, particularly as indicated by an increase in the interventricular mechanical delay, which may be indicative of progression of heart failure or other cardiovascular diseases.

Depending upon the capabilities of the pacer/ICD, any indication of progression of heart failure may be corroborated by other suitable detection techniques. See, for example, U.S. Pat. No. 6,922,587, entitled "System and Method for Tracking Progression of Left Ventricular Dysfunction Using Implantable Cardiac Stimulation Device", U.S. Pat. No. 6,942,622, entitled "Method For Monitoring Autonomic Tone", U.S. Pat. No. 6,748,261, entitled "Implantable Cardiac Stimulation Device For And Method Of Monitoring Progression Or Regression Of Heart Disease By Monitoring Interchamber Conduction Delays", U.S. Pat. No. 6,741,885, entitled "Implantable Cardiac Device For Managing The Progression Of Heart Disease And Method", U.S. Pat. No. 6,643,548, entitled "Implantable Cardiac Stimulation Device For Monitoring Heart Sounds To Detect Progression And Regression Of Heart Disease And Method Thereof", U.S. Pat. No. 6,572,557, entitled "System And Method For Monitoring Progression Of Cardiac Disease State Using Physiologic Sensors", U.S. Pat. No. 6,527,729, entitled "Method For Monitoring Patient Using Acoustic Sensor", U.S. Pat. No. 6,512,953, entitled "System And Method For Automatically Verifying Capture During Multi-Chamber Stimulation" and U.S. Pat. No. 6,480,733, entitled "Method For Monitoring Heart Failure", each assigned to Pacesetter, Inc. See, also, U.S. patent application Ser. No. 11/014,276, filed Dec. 15, 2004, of Bornzin et al., entitled "System and Method for Predicting a Heart Condition Based on Impedance Values Using an Implantable Medical Device", and U.S. patent application Ser. No. 10/792,305, filed Mar. 2, 2004, entitled "System And Method For Diagnosing And Tracking Congestive Heart Failure Based On The Periodicity Of Cheyne-Stokes Respiration Using An Implantable Medical Device", U.S. patent application Ser. No. 11/397,066 of Koh, entitled "QT-Based System and Method for Detecting and Distinguishing Dilated Cardiomyopathy and Heart Failure Using an Implantable Medical Device", also assigned to Pacesetter, Inc.

Exemplary Techniques

Figure 3:
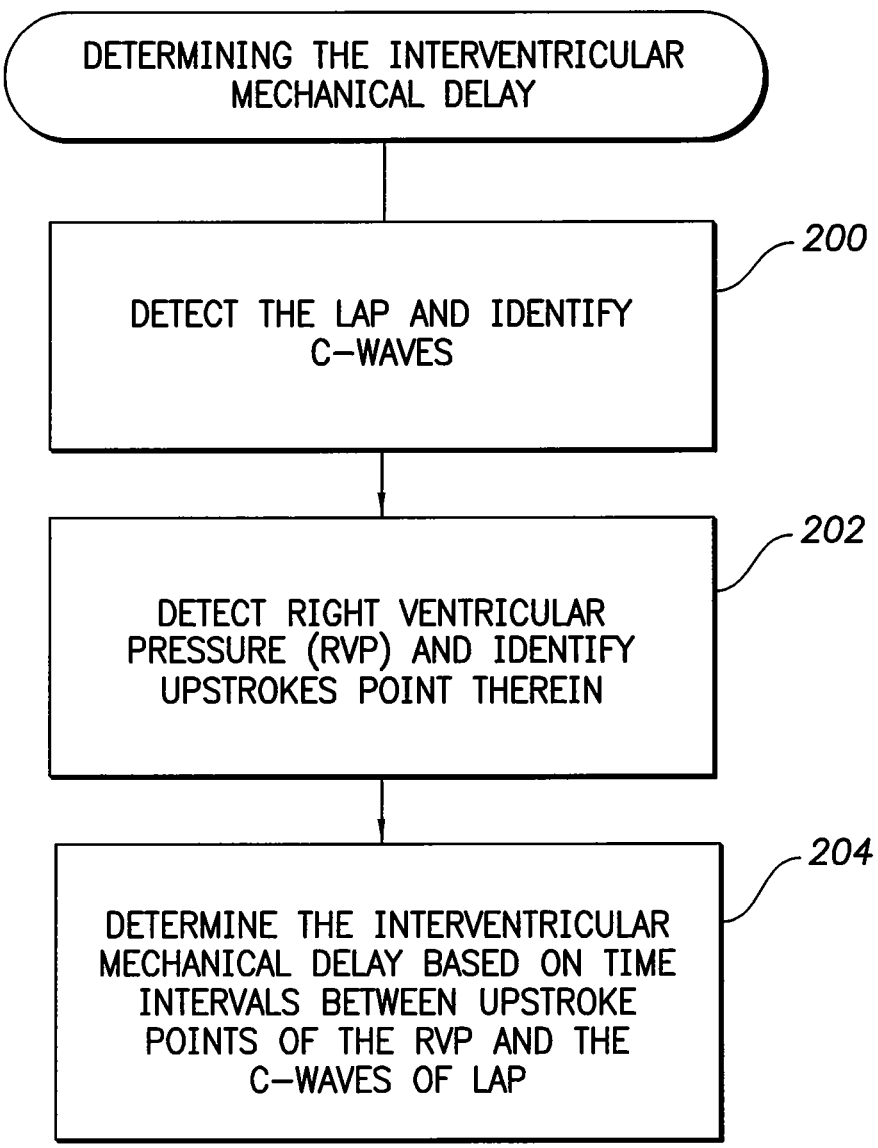
FIG. 3 illustrates an exemplary method for determining the interventricular mechanical delay in accordance with the general technique of FIG. 2 wherein RVP measurements are also exploited.

Turning now to FIGS. 3-7, various exemplary techniques for detecting ventricular mechanical or electromechanical delays or intervals based on LAP, alone or in combination with other detected signals will now be describes. FIG. 3 summarizes the exemplary technique for determining the interventricular mechanical delay, which, as noted, is the primary indicator of ventricular dyssynchrony. Beginning at step 200, the pacer/ICD detects the LAP and identifies c-waves therein. C-waves represent one of the features of the atrial pressure profile. At step 202, the pacer/ICD detects RVP and identifies upstrokes points therein. RVP may be detected using any suitable RVP sensor. See, for example, U.S. Pat. No. 6,915,162 to Noren et al., entitled "Implantable Medical Device for Measuring Ventricular Pressure". At step 204, the pacer/ICD determines the interventricular mechanical delay based on time intervals between upstroke points of the RVP and the c-waves of LAP.

Figure 4:
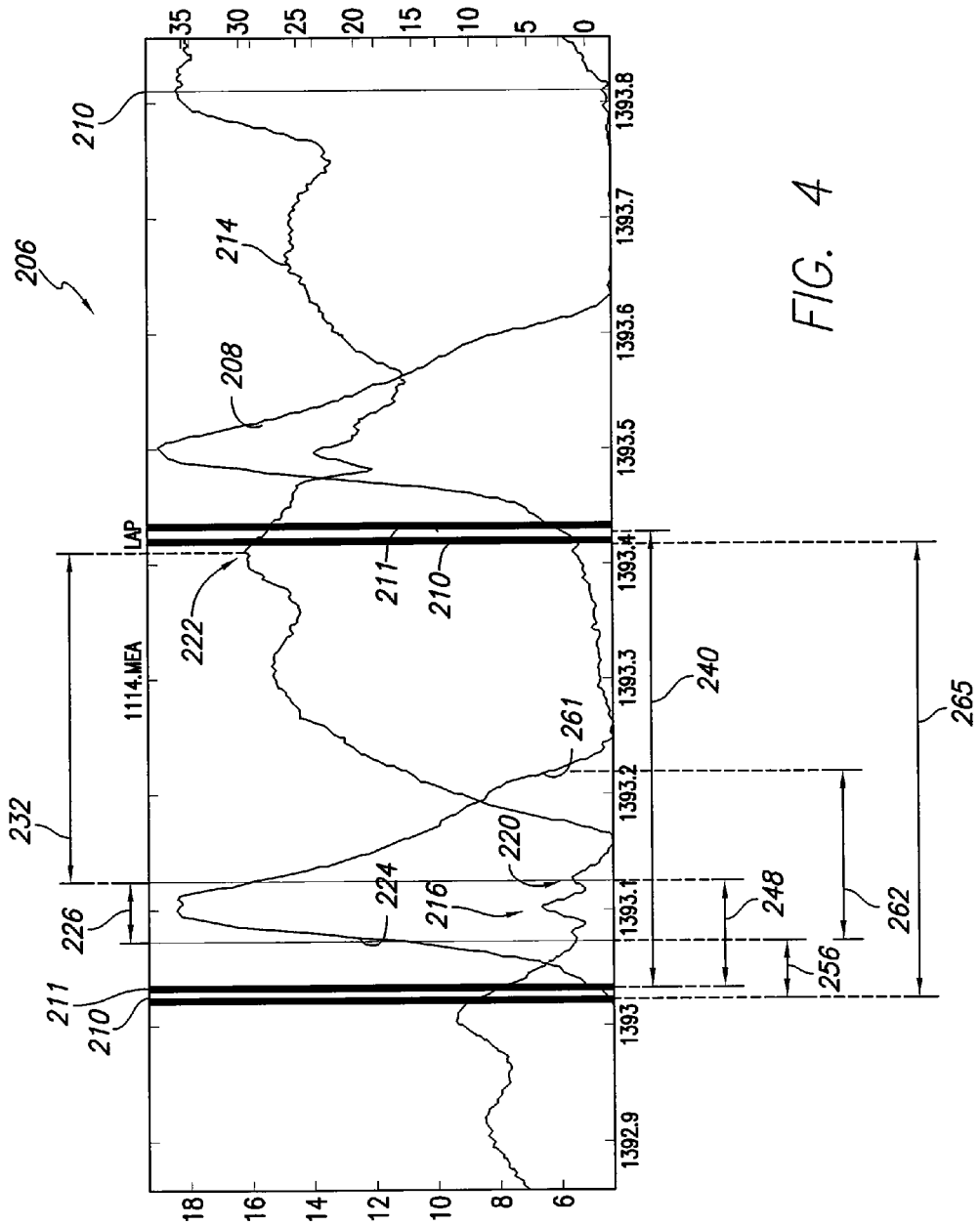
FIG. 4 provides exemplary graphs illustrating LAP and RVP sensor signals and other signals obtained from a patient with LBBB, which may be analyzed via the method of FIG. 3 to determine the interventricular mechanical delay.

Exemplary LAP and RVP signals are shown in FIG. 4 for a patient with LBBB. (The graph of FIG. 4 and any other graphs attached hereto are provided to illustrate features of the invention and should not be construed as necessarily being representative of clinical patient data. Actual LAP and RVP signals may differ in shape and magnitude within individual patients.) A graph 206 illustrates an RVP signal 208 along with vertical lines 210 marking $R_R$-waves (i.e. RV depolarization events) of an RV IEGM signal (not otherwise shown) and vertical lines 211 marking $R_L$-waves (i.e. LV depolarization events) of an LV IEGM signal (also not otherwise shown). As can be seen, there is a slight offset between the $R_R$-waves and the $R_L$-waves indicative of a slight delay between depolarization of the RV and subsequent depolarization of the LV. Note that, strictly speaking, an R-wave is a feature of the surface electrocardiogram (EKG). Herein, the term is used to refer to the corresponding feature of the IEGM, which is also referred to as the QRS-complex. R-waves are illustrated in the figure as they aid in locating the pertinent features of the LAP and RVP but do not necessarily need to be tracked while determining the interventricular mechanical delay, which, as noted, is determined based on LAP and RVP. The R-waves are also used in detecting other ventricular mechanical and electromechanical parameters, discussed below.

Graph 206 also illustrates a LAP signal 214. FIG. 4 also identifies the a-wave 216, the c-wave 220 and v-wave 222 of the LAP signal. Each cycle of the left atrial pressure waveform includes an a-wave, which is produced by an atrial contraction. Following the a-wave is a c-wave, which is produced by the left ventricle contracting against the closed mitral valve (MV). Following the c-wave is a v-wave, which is produced by the left ventricle end systole between the aortic valve closure and the mitral valve opening. For the purposes of determining the interventricular mechanical delay, the only feature of the LAP that needs to be detected is the c-wave. The other features of the LAP have been illustrated and described for the sake of completeness. In addition, some of these features are pertinent to detection of other ventricular mechanical and electromechanical parameters, as will be explained below. In any case, otherwise conventional signal processing techniques may be employed to identify the c-wave. Such techniques are well understood by those skilled in the art. Note that, if a readily identifiable c-wave is not present within the LAP, alternative (conventional) techniques may instead be employed by the pacer/ICD to detect the interventricular mechanical delay. Alternatively, detection of the interventricular mechanical delay may be deferred until a readily identifiable c-wave is again present within the patient. This applies as well to detection of other parameters described herein that exploit detection of the c-wave of the LAP.

Insofar as the upstroke of RVP is concerned (which is detected at step 202 of FIG. 3), graph 206 of FIG. 4 illustrates an exemplary upstroke point 224 along the RVP signal 208. The upstroke point may be defined as the point at which dP/dt of the RVP signal has its maximum positive value and conventional techniques may be used to identify this point. However, in other implementations, other points along the upstroke portion of the RVP curve may instead be used, so long as the system is consistent. For example, the point at which RVP just begins to increase or the point at which the increase in RVP ends may instead be used. In any case, at step 204 of FIG. 3, the pacer/ICD calculates the time delay or interval between upstroke point 224 of RVP signal 208 and c-wave 220 of LAP 214. This time delay, which is identified in FIG. 4 by reference numeral 226, is the interventricular mechanical delay. Generally speaking, the greater the interventricular mechanical delay, the greater the degree of ventricular dyssynchrony. In this particular example, the RV contracts prior to the LV by the time delay. In other cases, the LV may contract prior to the RV. If so, the c-wave of the LAP will occur before the upstroke point of the RVP. Preferably, the detected time delay values are averaged over some predetermined number of beats (or predetermined interval of time) to determine a suitable average. Trends in the interventricular mechanical delay (i.e. a sustained increase over a period of weeks or months) are preferably tracked at step 204, as well.

As the interventricular mechanical delay may vary based on heart rate or other factors such as respiration, the interventricular mechanical delay is preferably measured only while the patient is at rest. A sleep or circadian detector may be used to identify appropriate periods of time to measure the delay. Any of a variety of otherwise conventional sleep detection techniques may be employed. Examples are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device And Method For Varying Pacing Parameters To Mimic Circadian Cycles"; and in U.S. patent application Ser. No. 10/339,989 of Koh et al., entitled "System And Method For Detecting Circadian States Using An Implantable Medical Device", filed Jan. 10, 2003. In addition, posture detectors may be used to determine when the patient is in a certain predetermined posture (such as supine) so as to reduce or eliminate any variations in the measurement of the delay value that may be due to changes in posture. See, e.g., posture detection techniques described in U.S. Pat. No. 6,658,292 of Kroll et al., entitled "Detection of Patient's Position and Activity Status Using 3D Accelerometer-Based Position Sensor". See, also, U.S. patent application Ser. No. 10/329,233, of Koh et al., entitled "System and Method for Determining Patient Posture Based On 3-D Trajectory Using an Implantable Medical Device," filed Dec. 23, 2002.

Figure 5:
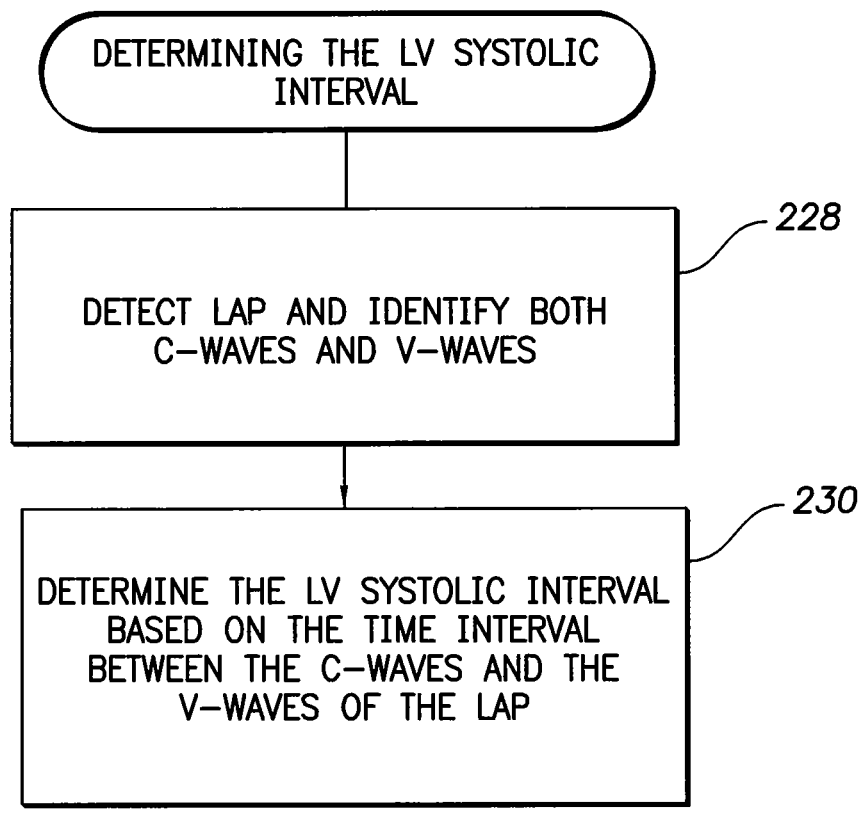
FIG. 5 illustrates an exemplary method for determining the LV systolic interval in accordance with the general technique of FIG. 2.

FIG. 5 summarizes the exemplary technique for determining the LV systolic interval. Beginning at step 228, the pacer/ICD detects the LAP and identifies c-waves and v-waves therein. At step 230, the pacer/ICD determines the LV systolic interval based on time intervals between the c-waves of LAP and the v-waves of the LAP. That is, the time delay between the c-wave and the next v-wave (i.e. the c-v interval), which is identified in FIG. 4 by reference numeral 232, is equated with the LV systolic interval.

Figure 6:
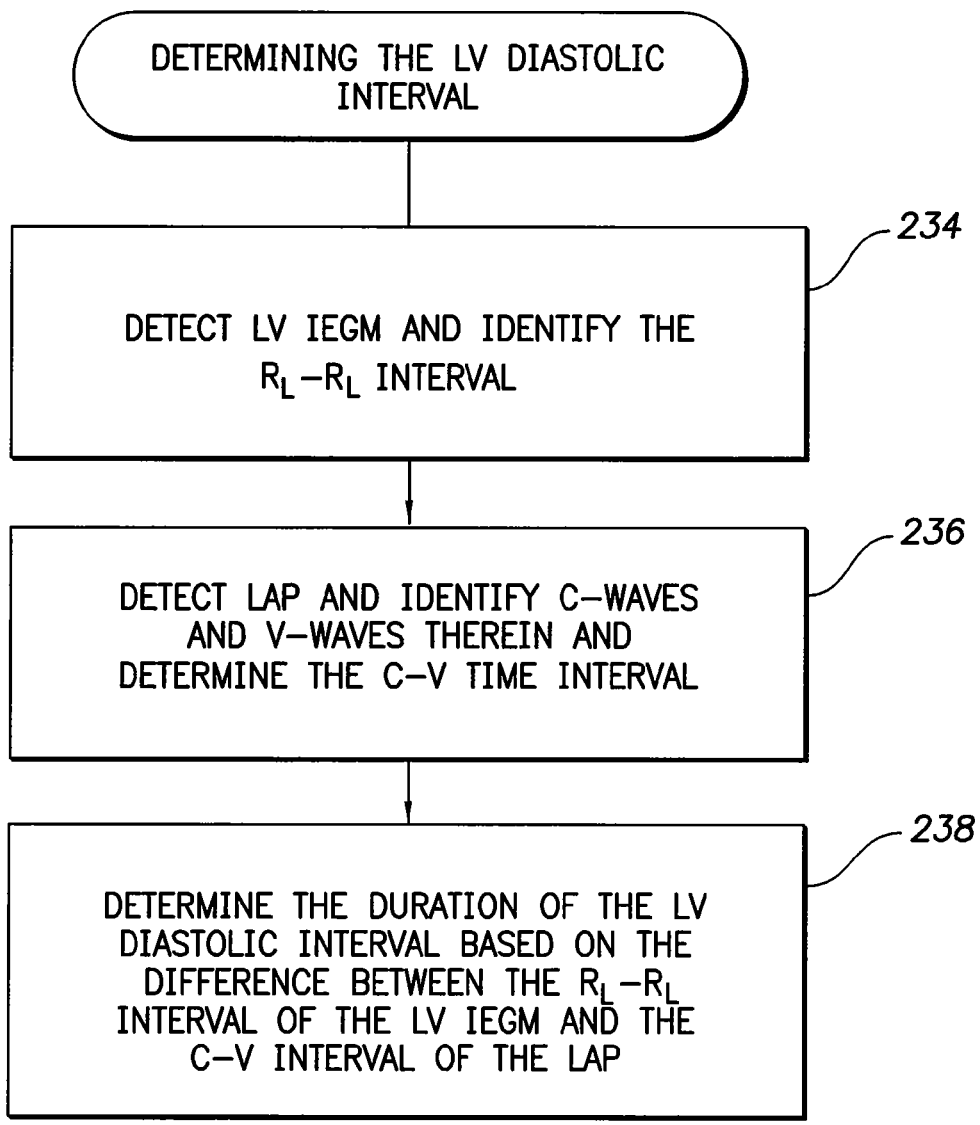
FIG. 6 illustrates an exemplary method for determining the LV diastolic interval in accordance with the general technique of FIG. 2.

FIG. 6 summarizes the exemplary technique for determining the LV diastolic interval. Beginning at step 234, the pacer/ICD detects the LV IEGM and identifies the $R_L$-$R_L$ interval therein, i.e. the interval between successive R-waves detected using at least one LV electrode. An exemplary $R_L$-$R_L$ interval 240 is shown in FIG. 4. Depending upon the implementation, the LV IEGM may be detected using bipolar sensing (i.e. between tip and ring LV electrodes) or via unipolar sensing (i.e. between an LV tip electrode and the device housing, or between the LV electrodes and the RV coil, if present.) At step 236, the pacer/ICD detects the LAP, identifies c-waves and v-waves and determines the c-v interval (which, as already noted, represents the LV systolic interval). At step 230, the pacer/ICD then determines the duration of the LV diastolic interval based on the difference between the $R_L$-$R_L$ interval of the LV IEGM and c-v interval of the LAP. In other words, the duration of the LV diastolic interval is the duration of the $R_L$-$R_L$ interval 240 minus the duration of the LV systolic interval 232.

Figure 7:
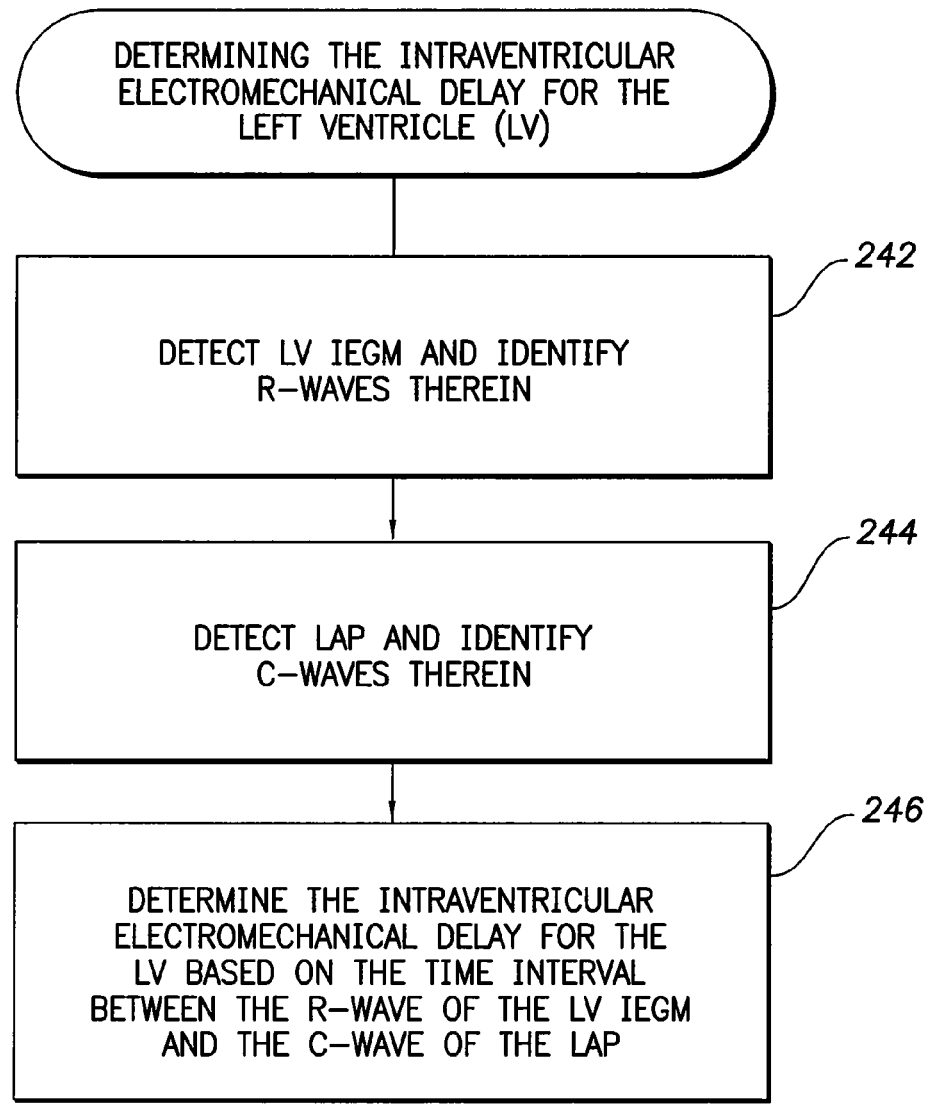
FIG. 7 illustrates an exemplary method for determining the intraventricular electromechanical delay for the LV in accordance with the general technique of FIG. 2 wherein LV IEGM signals are also exploited.

FIG. 7 summarizes the exemplary technique for determining the intraventricular electromechanical delay for the LV. Beginning at step 242, the pacer/ICD detects the LV IEGM and identifies the $R_L$-waves therein. At step 244, the pacer/ICD detects the LAP and identifies c-waves therein. At step 246, the pacer/ICD then determines the intraventricular electromechanical delay for the LV based on the difference between the location of the $R_L$-wave and c-wave of the LAP. That is, the time delay between the R-wave of the LV IEGM and the subsequent c-wave, which is identified in FIG. 4 by reference numeral 248, is equated with the intraventricular electromechanical delay for the LV.

Figure 8:
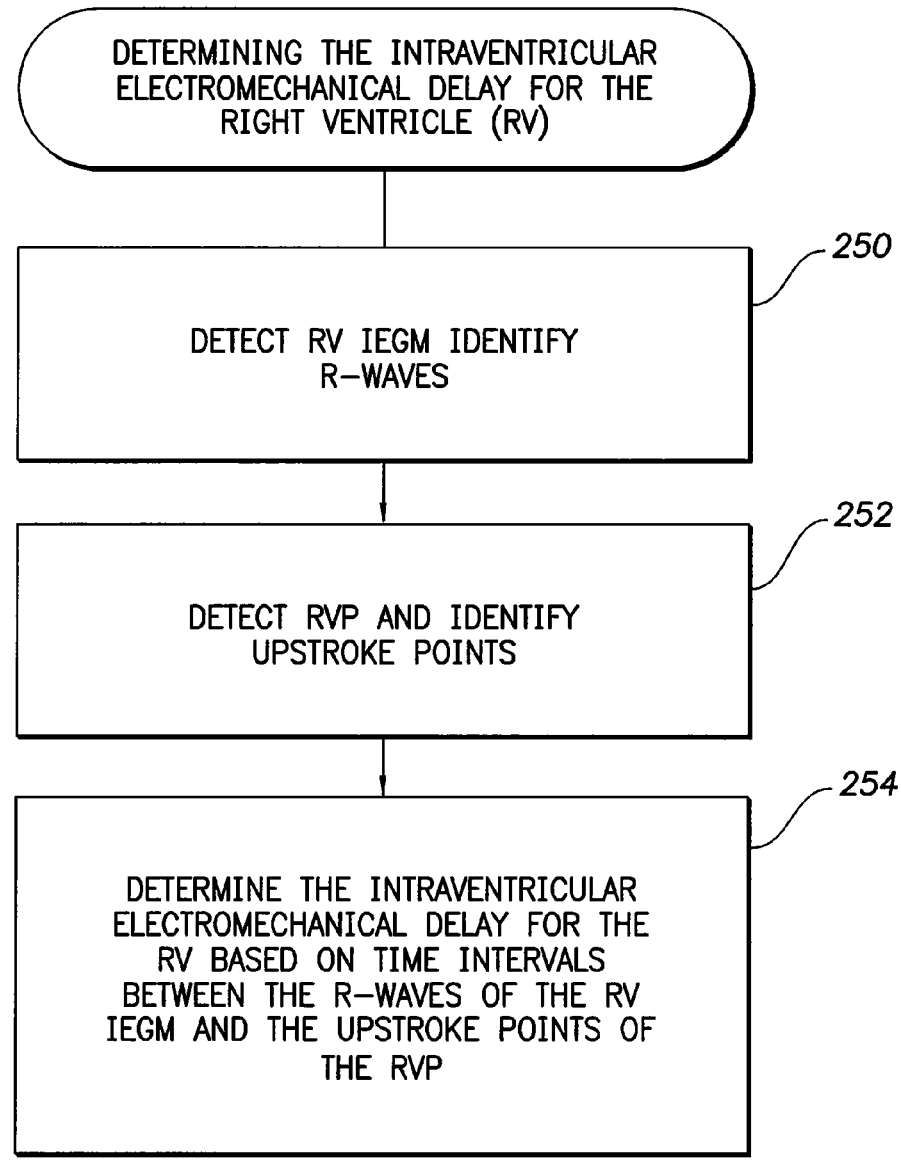
FIG. 8 illustrates an exemplary method for determining the intraventricular electromechanical delay for the RV for use in addition to the general technique of FIG. 2 wherein RVP and RV IEGM signals are also exploited.

FIG. 8 summarizes the exemplary technique for determining the intraventricular electromechanical delay for the RV. Beginning at step 250, the pacer/ICD detects the RV IEGM and identifies the $R_R$-waves therein. As with the LV IEGM, the RV IEGM may be detected using bipolar sensing (i.e.

between tip and ring electrodes both implanted in the RV) or via unipolar sensing (i.e. between a RV tip electrode and the device housing.) At step 252, the pacer/ICD detects the RVP and identifies upstroke points therein. At step 254, the pacer/ICD then determines the intraventricular electromechanical delay for the RV based on the difference between the location of the $R_R$-wave and the upstroke point of the RVP. That is, the time delay between the R-wave of the RV IEGM and the next RV upstroke, which is identified in FIG. 4 by reference numeral 256, is equated with the intraventricular electromechanical delay for the RV. Note that, unlike the parameters discussed above, detection of the intraventricular electromechanical delay for the RV does not exploit detection of the LAP and hence can be performed by device that do not include a LAP sensor.

Figure 9:
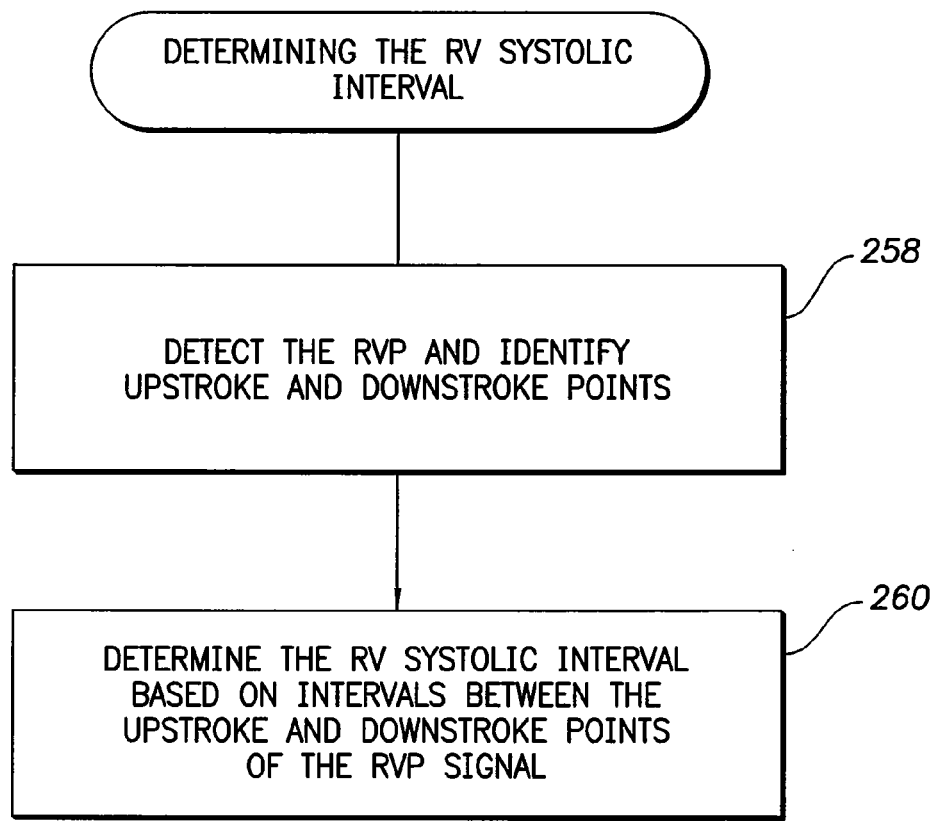
FIG. 9 illustrates an exemplary method for determining the RV systolic interval for use in addition to the general technique of FIG. 2 wherein RVP signals are also exploited.

FIG. 9 summarizes the exemplary technique for determining the RV systolic interval. Beginning at step 258, the pacer/ICD detects the RVP and identifies upstroke and downstroke points therein. As noted above, the upstroke point may be defined as the point at which dP/dt of the RVP signal is at its maximum. Likewise, the downstroke point may be defined as the point at which dP/dt of the RVP signal has its maximum negative value. Alternatively, as with detecting the upstroke of the RVP, other points along the downstroke portion of the RVP curve may instead be used, so long as the system is consistent. For example, the point at which RVP just begins to decrease or the point at which the decrease in RVP ends may instead be used. An exemplary downstroke points is identified in FIG. 4 by reference numeral 261. At step 260, the pacer/ICD then determines the RV systolic interval based on the difference between the upstroke and downstroke points of the RVP. This interval is identified in FIG. 4 by reference numeral 262. As with determining the intraventricular electromechanical delay for the RV, detection of the RV systolic interval does not exploit detection of the LAP and hence can be performed by device that do not include a LAP sensor.

Figure 10:
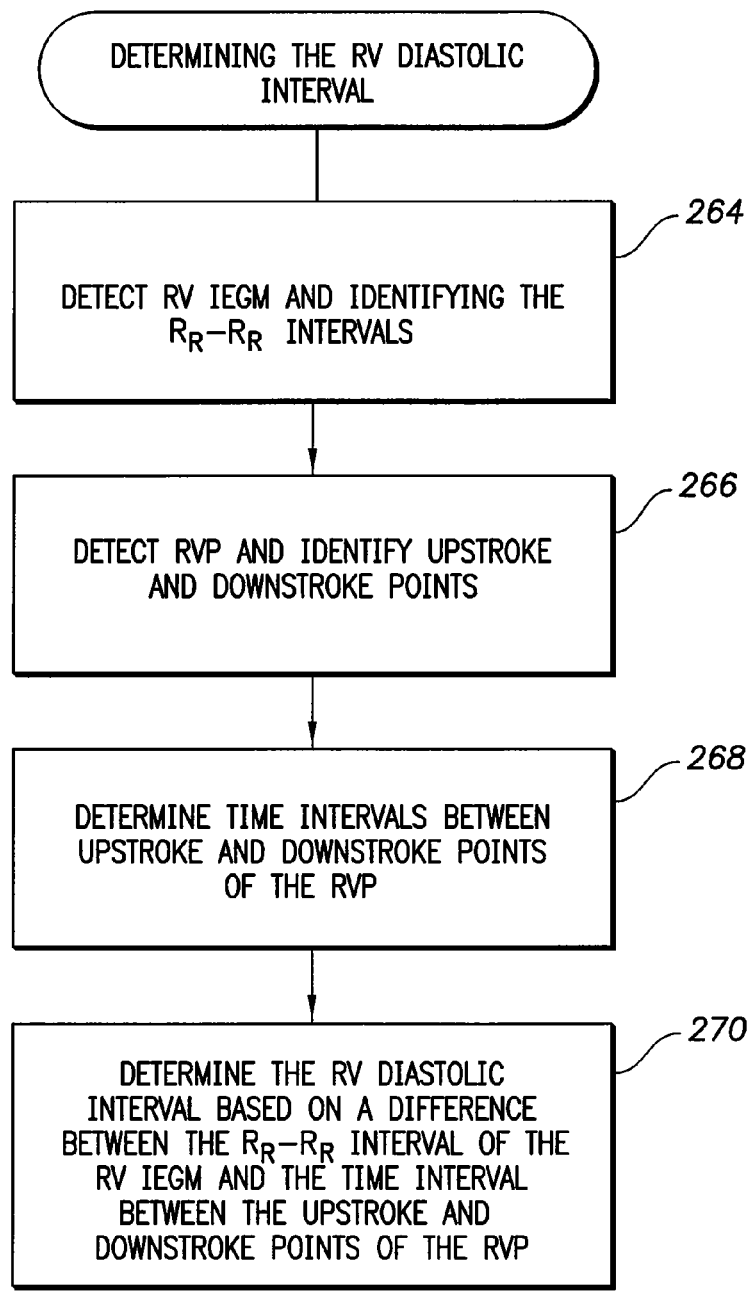
FIG. 10 illustrates an exemplary method for determining the RV diastolic interval for use in addition to the general technique of FIG. 2 wherein RVP and RV IEGM signals are also exploited.

FIG. 10 summarizes the exemplary technique for determining the RV diastolic interval. Beginning at step 264, the pacer/ICD detects the RV IEGM and identifies the $R_R$-$R_R$ interval therein, i.e. the interval between successive R-waves detected using at least one electrode implanted in the RV. An exemplary $R_R$-$R_R$ interval 265 is shown in FIG. 4. At step 266, the pacer/ICD detects, the pacer/ICD detects the RVP and identifies upstroke and downstroke points therein. At step 268, the pacer/ICD determines the time intervals between the RVP upstroke and downstroke points. At step 270, the pacer/ICD then determines the duration of the RV systolic interval based on the difference between the duration of the $R_R$-$R_R$ interval of the RV IEGM and duration between the upstroke and downstroke points of the RVP. In other words, the duration of the RV diastolic interval is the duration of the $R_R$-$R_R$ interval 265 minus the duration of the RV systolic interval 262. What have been presented thus far are examples where individual ventricular contraction intervals are separately evaluated. Preferably, though, the pacer/ICD is equipped to determine each of the aforementioned parameters.

Figure 11:
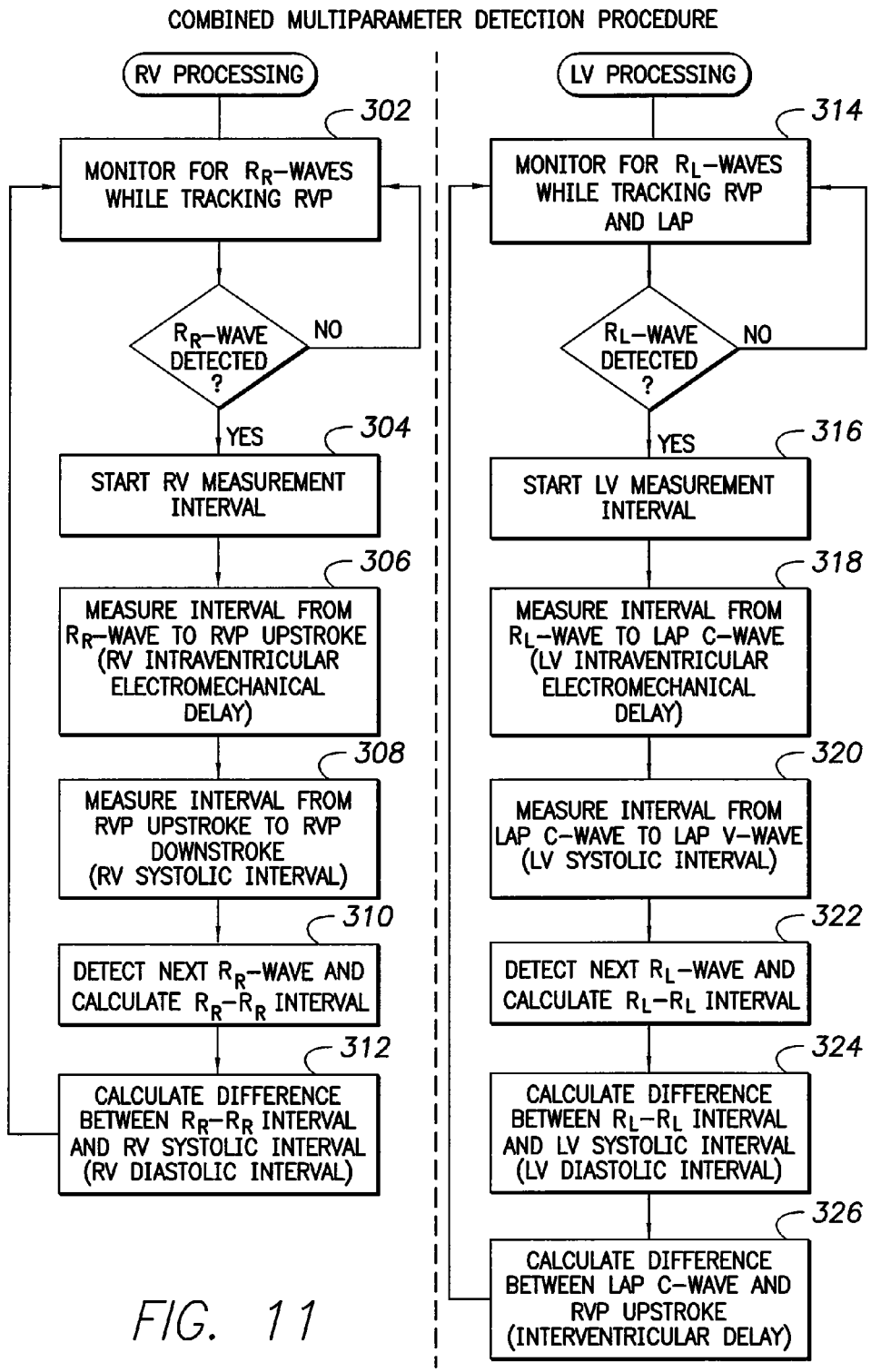
FIG. 11 illustrates an exemplary combined method for determining each of the various parameters pertinent to ventricular dyssynchrony for use with the general technique of FIG. 2.

FIG. 11 summarizes a combined multiparameter detection technique. For RV processing, beginning at step 302, the pacer/ICD monitors for $R_R$-waves while also tracking RVP. When the next $R_R$-wave is detected, the pacer/ICD begins tracking an RV measurement interval, step 304. The interval between the $R_R$-wave and the next upstroke point of the RVP is measured, step 306, which is the RV electromechanical delay (described separately above with reference to FIG. 8). The interval between the RVP upstroke point and the next RVP downstroke point is then measured, step 308, which is the RV systolic interval (described separately above with reference to FIG. 9). At step 310, the pacer/ICD then detects the next $R_R$-wave and calculates the $R_R$-$R_R$ interval. The difference between the $R_R$-$R_R$ interval and the RV systolic interval is then calculated, step 312, which is the RV diastolic interval (described separately above with reference to FIG. 10).

Concurrently, LV is also preformed. At step 314, the pacer/ICD monitors for $R_L$-waves while also tracking RVP and LAP. When the next $R_L$-wave is detected, the pacer/ICD begins tracking an LV measurement interval, step 316. The interval between the $R_L$-wave and the c-wave of the LAP is measured, step 318, which is the LV electromechanical delay (described separately above with reference to FIG. 7). The interval between the LAP c-wave and the LAP v-wave is then measured, step 320, which is the LV systolic interval (described separately above with reference to FIG. 5). At step 322, the pacer/ICD then detects the next $R_L$-wave and calculates the $R_L$-$R_L$ interval. The difference between the $R_L$-$R_L$ interval and the LV systolic interval is then calculated, step 324, which is the LV diastolic interval (described separately above with reference to FIG. 6). Finally, the difference between the LAP c-wave and the RVP upstroke point is calculated, step 326, which is the interventricular mechanical delay (described separately above with reference to FIG. 3).

What have been described are various techniques for detecting ventricular mechanical and electromechanical delay values. For the sake of completeness, a detailed description of an exemplary pacer/ICD for controlling these functions will now be provided. However, principles of invention may be implemented within other pacer/ICD implementations or within other implantable devices. In addition, principles of the invention may also be applicable to detecting certain atrial mechanical and electromechanical delay intervals as well. Furthermore, although examples described herein involve processing of the various signals by the implanted device itself, some operation may be performed using an external device. For example, recorded IEGM, RVP and LAP data may be transmitted to an external device, which processes the data to evaluate interventricular delay, etc. Processing by the implanted device itself is preferred as that allows prompt changes pacing control parameters to address any changes in the various detected delay values.

Exemplary Pacemaker/ICD

Figure 12:
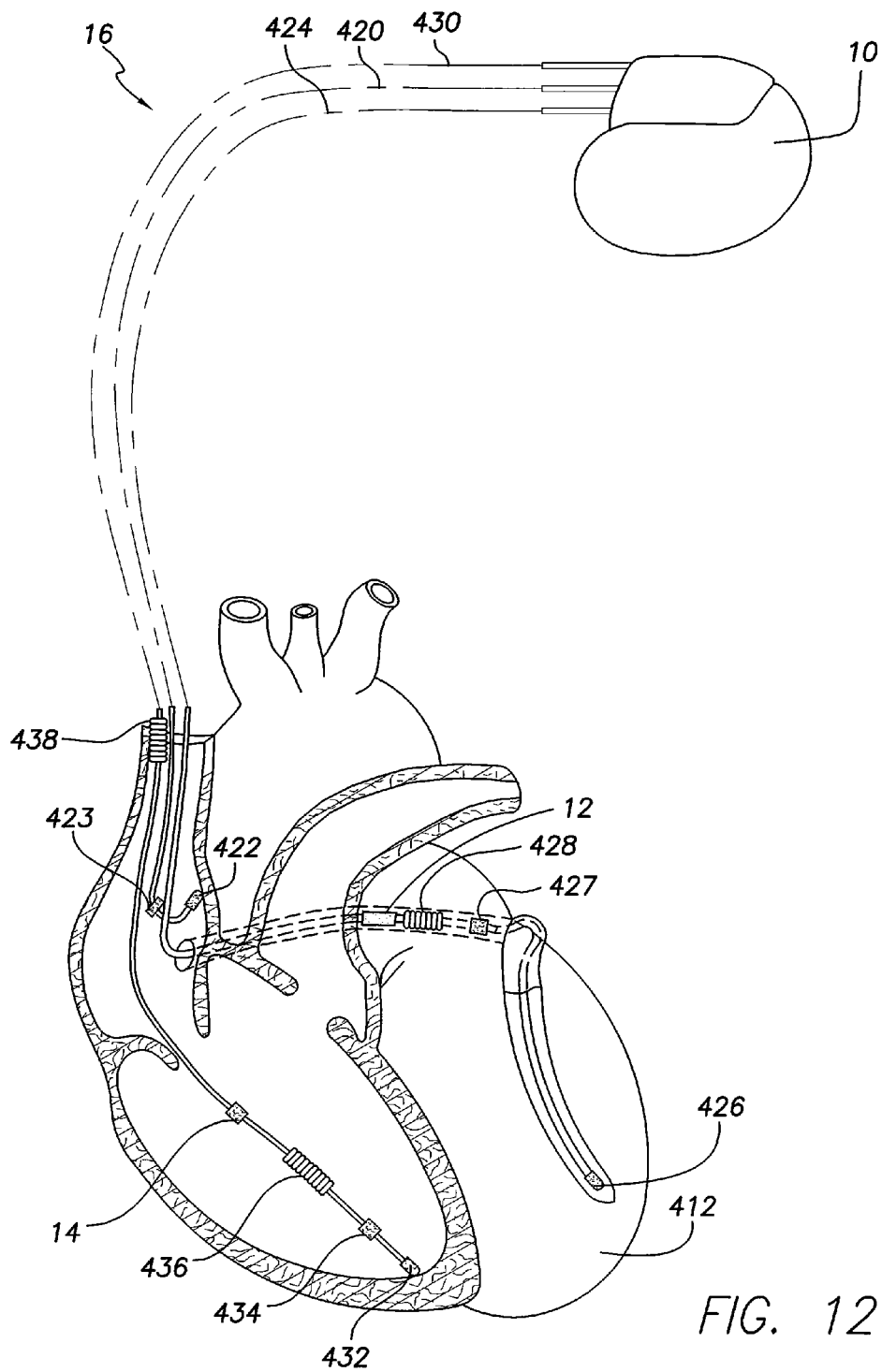
FIG. 12 is a simplified, partly cutaway view, illustrating the pacer/ICD of FIG. 1 along with a complete set of exemplary leads implanted in the heart of a patient.

FIG. 12 provides a simplified block diagram of the pacer/ICD, which is a multi-chamber stimulation device capable of treating both fast and slow arrhythmias with stimulation therapy, including cardioversion, defibrillation, and pacing stimulation, as well as being capable of tracking the various ventricular delay intervals discussed above and controlling therapy in response thereto. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 418 is transvenously inserted into the heart to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 12, it should also be understood that additional stimulation leads (with one or more pacing, sensing and/or shocking electrodes) might be used in order to efficiently and effectively provide pacing stimulation to the left side of the heart or atrial cardioversion and/or defibrillation.

In addition to the various electrodes already described, the lead system also provides an RVP sensor 14 and an LAP sensor 12. As can be seen, the RVP sensor is mounted along RV lead 430 within the RV. LAP sensor 12 is mounted adjacent the left atrial coil electrode 428 along CS lead 424. Alternatively, a separate lead may be provided for positioning the LAP sensor adjacent the left atrium. In still other implementations, the CS lead is split, within one portion extending adjacent the left atrium (where the LAP sensor is positioned) and the other portion continuing adjacent the left ventricle (where the LV tip and ring electrodes are positioned.) Lead systems incorporating LAP sensors are discussed in various patents and patent applications cited above, particularly Eigler et al., Hedberg, and the applications of Mann et al. Lead systems incorporating RVP sensors are discussed in various other patents and patent applications cited above, particularly Noren et al. Those skilled in the art can readily modify the lead system illustrated in FIG. 12 as needed to provide for accurate LAP and RVP sensing, depending upon the characteristics of the particular LAP sensor and the needs of the patient. Furthermore, an LVP sensor may additionally be provided for implant along the CS lead adjacent the LV. LVP sensors are described in U.S. Pat. No. 6,666,826 to Salo, et al., entitled "Method and apparatus for measuring left ventricular pressure".

Figure 13:
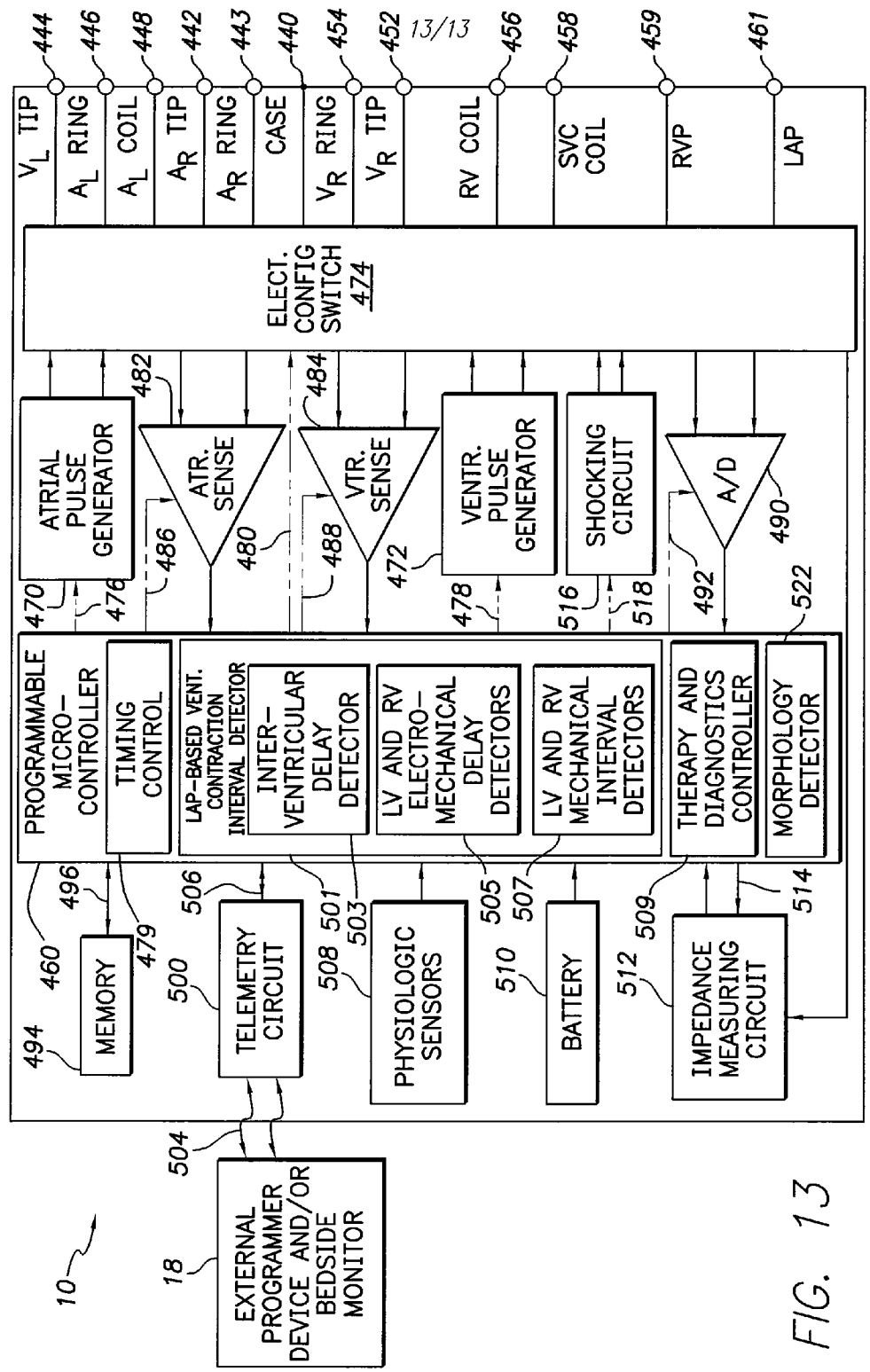
FIG. 13 is a functional block diagram of the pacer/ICD of FIG. 12, illustrating basic circuit elements that provide cardioversion, defibrillation and/or pacing stimulation in four chambers of the heart and particularly illustrating components for evaluating ventricular dyssynchrony and for controlling therapy in response thereto.

A simplified block diagram of internal components of pacer/ICD 10 is shown in FIG. 13. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 440 for pacer/ICD 10, shown schematically in FIG. 13, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

Additionally, an RVP terminal 459 is illustrated for receiving signals from RVP sensor 14. A LAP terminal 461 is illustrated for receiving signals from LAP sensor 12. Depending upon the characteristics of the particular sensors being used, additional terminals may be needed to accommodate the sensors.

At the core of pacer/ICD 10 is microcontroller 104, which controls the various modes of stimulation therapy. As is well known in the art, the microcontroller 104 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 104 includes the ability to process or monitor input signals (data) as controlled by a program code stored in a designated block of memory. The details of the design and operation of the microcontroller 104 are not critical to the invention. Rather, any suitable microcontroller 104 may be used that carries out the functions described herein. The use of microprocessor-based control circuits for performing timing and data analysis functions are well known in the art.

As shown in FIG. 13, an atrial pulse generator 470 and a ventricular pulse generator 472 generate pacing stimulation pulses for delivery by the right atrial lead 420, the right ventricular lead 418, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 104 via appropriate control signals, 476 and 478, respectively, to trigger or inhibit the stimulation pulses.

The microcontroller 104 further includes timing control circuitry (not separately shown) used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 104, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 418, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain control and/or automatic sensitivity control enables pacer/ICD 10 to deal effectively with the difficult problem of sensing the low amplitude signal characteristics of atrial or ventricular fibrillation. The outputs of the atrial and ventricular sense amplifiers may be in the form of interrupts. The microcontroller 104 triggers or inhibits the atrial and ventricular pulse generators, 470 and 472, respectively, in a demand fashion in response to the absence or presence of cardiac activity in the appropriate chambers of the heart, as represented by the atrial and ventricular event interrupts.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 104 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 418 through the switch 474 to sample cardiac signals across any pair of desired electrodes. The microcontroller 104 is further coupled to a memory 494 by a suitable data/address bus 496, wherein the programmable operating parameters used by the microcontroller 104 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Microcontroller 60 also includes various components for controlling the various operations described above with reference to FIGS. 1-11. In particular, the microcontroller includes a LAP-based ventricular contraction interval detector 501 operative to determine at least one ventricular contraction interval based in part on an LAP signal detected by LAP detector 12 alone or in combination with other detected signals, such as signals from RVP detector 14. The LAP-based ventricular contraction interval detector is also referred to herein as a LAP-based ventricular dyssynchrony evaluation system. Detector 501 includes an interventricular delay detector 503 operative to detect the interventricular delay in accordance with techniques described above with reference to FIG. 3. Detector 501 also includes an LV and RV electromechanical delay detector 505 operative to detect the LV and RV electromechanical delays in accordance with techniques described above with reference to FIGS. 7 and 8. Detector 501 further includes an LV and RV mechanical delay detector 507 operative to detect the LV and RV mechanical delays (such as LV systolic intervals, RV diastolic intervals, etc.) in accordance with techniques described above with reference to FIGS. 5-6 and 9-10. The microcontroller also includes a therapy and diagnostic controller 508 operative to control therapy in response to any or all of the various ventricular contraction parameters detected as well as to control recording of appropriate diagnostic information within memory 494 pertinent to the particular ventricular contraction parameters detected and to ventricular dyssynchrony in general.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 104 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 104 responds by adjusting the various pacing parameters (such as rate, AV delay, V-V delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 13. The battery 510 may vary depending on the capabilities of pacer/ICD 10. If the system only provides low-voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, pacer/ICD 10 is preferably capable of high-voltage therapy and appropriate batteries.

As further shown in FIG. 13, pacer/ICD 10 is shown as having an impedance measuring circuit 512 which is enabled by the microcontroller 104 via a control signal 514. Impedance values may also be used for tracking respiration; for surveillance during the acute and chronic phases for proper lead positioning or dislodgement; for measuring respiration or minute ventilation; for measuring thoracic impedance for use in setting shock thresholds; for detecting when the device has been implanted; and for detecting the opening of heart valves, etc. The impedance measuring circuit 120 is advantageously coupled to the switch 74 so that any desired combination of electrodes may be used.

In the case where pacer/ICD 10 is intended to operate as an ICD, it detects the occurrence of an arrhythmia, and automatically applies an appropriate electrical shock therapy to the heart aimed at terminating the detected arrhythmia. To this end, the microcontroller 104 further controls a shocking circuit 516 by way of a control signal 518. The shocking circuit 516 generates shocking pulses of low (up to 0.5 joules), moderate (0.5-10 joules) or high energy (11 to 40 joules or more), as controlled by the microcontroller 104. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with a VS event and/or pertaining to the treatment of tachycardia. Defibrillation shocks are generally of moderate to high energy level (i.e., corresponding to thresholds in the range of 5-40 joules), delivered asynchronously (since VS events may be too disorganized), and pertaining exclusively to the treatment of fibrillation. Accordingly, the microcontroller 104 is capable of controlling the synchronous or asynchronous delivery of the shocking pulses.

In addition, the stimulation device may be configured to perform automatic mode switching (AMS) wherein the pacemaker automatically reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The principles of the invention may be exploiting using other implantable systems or in accordance with other techniques. Thus, while the invention has been described with reference to particular exemplary embodiments, modifications can be made thereto without departing from scope of the invention. The various functional components of the exemplary systems described herein may be implemented using any appropriate technology including, for example, microprocessors running software programs or application specific integrated circuits (ASICs) executing hard-wired logic operations. Note also that the term "including" as used herein is intended to be inclusive, i.e. "including but not limited to".

What is claimed is:

1. A system for use with an implantable medical device for determining ventricular contraction intervals, the system comprising:
   means for detecting a left atrial pressure (LAP) signal;
   means for identifying a c-wave and a v-wave in the LAP signal;
   means for determining a left ventricular (LV) systolic interval based in part on a time interval between the c-wave and the v-wave of the LAP signal; and
   means for modifying therapy delivered by the implantable medical device based on the LV systolic interval.

2. A system for use with an implantable medical device for determining ventricular contraction intervals, the system comprising:
   means for detecting a left atrial pressure (LAP) signal;
   means for detecting a left ventricular (LV) electrical cardiac signal using at least one LV electrode;
   means for determining a left ventricular diastolic interval based on a comparison of the LAP signals and the LV electrical cardiac signal; and
   means for modifying therapy delivered by the device based on the LV diastolic interval.

3. The system of claim 2 wherein the means for detecting the LV electrical cardiac signal comprises means for identifying an $R_L$-$R_L$ interval therein and wherein the means for detecting the LAP signal includes means for identifying both a c-wave and a v-wave therein and for determining a c-v time interval therebetween and wherein the means for determining the LV diastolic interval comprises means for determining the LV diastolic interval based on a difference between the $R_L$-$R_L$ interval of the LV electrical signal and the c-v time interval of the LAP.

4. A method for use with an implantable media device for determining ventricular contraction intervals, the method comprising
   detecting a left atrial pressure (LAP) signal;
   identifying a c-wave and a v-wave in the LAP signal;
   determining a left ventricular (LV) systolic interval based at least in part on a time interval between the c-wave and the v-wave of the LAP signal;
   modifying therapy delivered by the implantable medical device based on the LV systolic interval.

5. A method for use with an implantable medical device for determining ventricular contraction intervals, the method comprising
   detecting a left atrial pressure (LAP) signal;
   detecting a left ventricular (LV) electrical cardiac signal using at least one LV electrode;
   determining a left ventricular diastolic interval based on a comparison of the LAP signals and the LV electrical cardiac signal; and modifying therapy delivered by the implantable medical device based on the left ventricular diastolic interval.

6. The method of claim 5 wherein detecting the LV electrical cardiac signal comprises identifying an $R_L$-$R_L$ interval therein and wherein detecting the LAP signal includes identifying both a c-wave and a v-wave therein and determining a c-v time interval therebetween and wherein determining the LV diastolic interval comprises determining the LV diastolic interval based on a difference between the $R_L$-$R_L$ interval of the LV electrical signal and the c-v time interval of the LAP.

* * * * *